United States Patent
Geisz (12)

(10) Patent No.: US 11,896,262 B2
(45) Date of Patent: Feb. 13, 2024

(54) METHOD AND SYSTEM FOR GAS MAINTENANCE TO A BODY CAVITY USING A TROCAR

(71) Applicant: Lexion Medical, LLC, St. Paul, MN (US)

(72) Inventor: Carl M. Geisz, Edina, MN (US)

(73) Assignee: LEXION MEDICAL, LLC, St. Paul, MN (US)

( * ) Notice: Subject to any disclaimer, the term of this patent is extended or adjusted under 35 U.S.C. 154(b) by 418 days.

(21) Appl. No.: 17/009,271

(22) Filed: Sep. 1, 2020

(65) Prior Publication Data
US 2020/0397468 A1 Dec. 24, 2020

Related U.S. Application Data

(63) Continuation of application No. 16/271,072, filed on Feb. 8, 2019, now Pat. No. 10,799,266, which is a continuation-in-part of application No. 14/792,873, filed on Jul. 7, 2015, now Pat. No. 10,238,421.

(51) Int. Cl.
*A61B 17/34* (2006.01)
*A61M 16/10* (2006.01)
*A61M 13/00* (2006.01)

(52) U.S. Cl.
CPC ...... *A61B 17/3421* (2013.01); *A61B 17/3474* (2013.01); *A61B 17/3417* (2013.01); *A61B 2218/008* (2013.01); *A61M 13/003* (2013.01); *A61M 13/006* (2014.02); *A61M 16/105* (2013.01); *A61M 2205/3344* (2013.01)

(58) Field of Classification Search
CPC ......... A61B 17/3474; A61B 2218/008; A61M 13/003
See application file for complete search history.

(56) References Cited

U.S. PATENT DOCUMENTS

| 4,481,008 A | 11/1984 | Kurtz |
| 5,159,921 A * | 11/1992 | Hoover .............. A61B 17/0293 600/245 |
| 5,209,721 A | 5/1993 | Wilk |

(Continued)

FOREIGN PATENT DOCUMENTS

WO  WO2012128826 A3  9/2012

OTHER PUBLICATIONS

United States Patent and Trademark Office, Notice of Allowance and Fee(s) Due; U.S. Appl. No. 16/271,072, filed Feb. 8, 2019.

*Primary Examiner* — Courtney B Fredrickson
(74) *Attorney, Agent, or Firm* — BAKER BOTTS L.L.P.

(57) ABSTRACT

According to one embodiment, a trocar assembly having a proximal end and a distal end comprises an inner tubular member and an outer tubular member. The inner tubular member is formed with an opening at the proximal end and an opening at the distal end, the openings adapted to provide access for one or more surgical instruments during a surgical procedure. The outer tubular member is disposed about the inner tubular member, the outer tubular member being partitioned into at least a first chamber and a second chamber, wherein: the inner tubular member is separated from the outer tubular member by an inner wall; the first chamber is separated from the second chamber; and the first chamber and the second chamber are defined by the inner wall and an outer wall of the outer tubular member.

4 Claims, 8 Drawing Sheets

(56) References Cited

U.S. PATENT DOCUMENTS

| | | | |
|---|---|---|---|
| 5,328,458 | A | 7/1994 | Sekino et al. |
| 6,905,489 | B2 | 6/2005 | Mantell et al. |
| 7,285,112 | B2 * | 10/2007 | Stubbs ............... A61B 17/3421 |
| | | | 604/23 |
| 7,722,558 | B2 | 5/2010 | Ott |
| 8,216,189 | B2 | 7/2012 | Stubbs et al. |
| 8,715,219 | B2 | 5/2014 | Stearns et al. |
| 2004/0204671 | A1 | 10/2004 | Stubbs et al. |
| 2004/0254524 | A1 * | 12/2004 | Spearman ........... A61M 16/142 |
| | | | 604/26 |
| 2005/0171465 | A1 * | 8/2005 | Smith ................ A61B 17/3496 |
| | | | 604/26 |
| 2005/0288622 | A1 | 12/2005 | Albrecht et al. |
| 2006/0025749 | A1 | 2/2006 | Moenning |
| 2007/0088275 | A1 | 4/2007 | Stearns et al. |
| 2009/0221963 | A1 * | 9/2009 | Lloyd ................... A61B 18/00 |
| | | | 604/119 |
| 2010/0241061 | A1 * | 9/2010 | Ott ..................... A61B 17/3421 |
| | | | 604/167.03 |
| 2011/0071359 | A1 | 3/2011 | Bonadio et al. |
| 2011/0178413 | A1 | 7/2011 | Schmitt et al. |
| 2012/0316510 | A1 * | 12/2012 | Ott ..................... A61B 17/3421 |
| | | | 604/246 |
| 2012/0316512 | A1 | 12/2012 | Ott et al. |
| 2015/0359666 | A1 | 12/2015 | Zacharias |

* cited by examiner

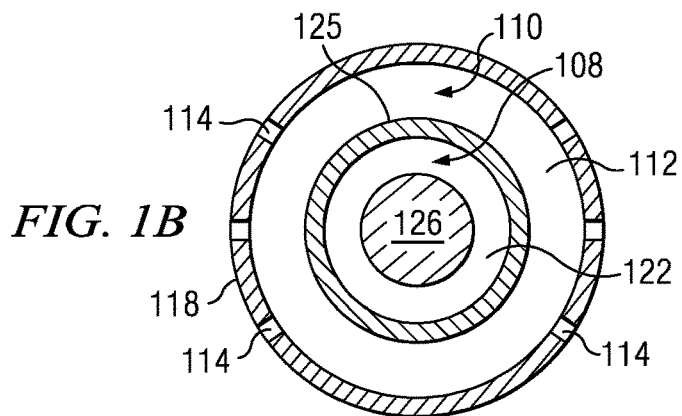
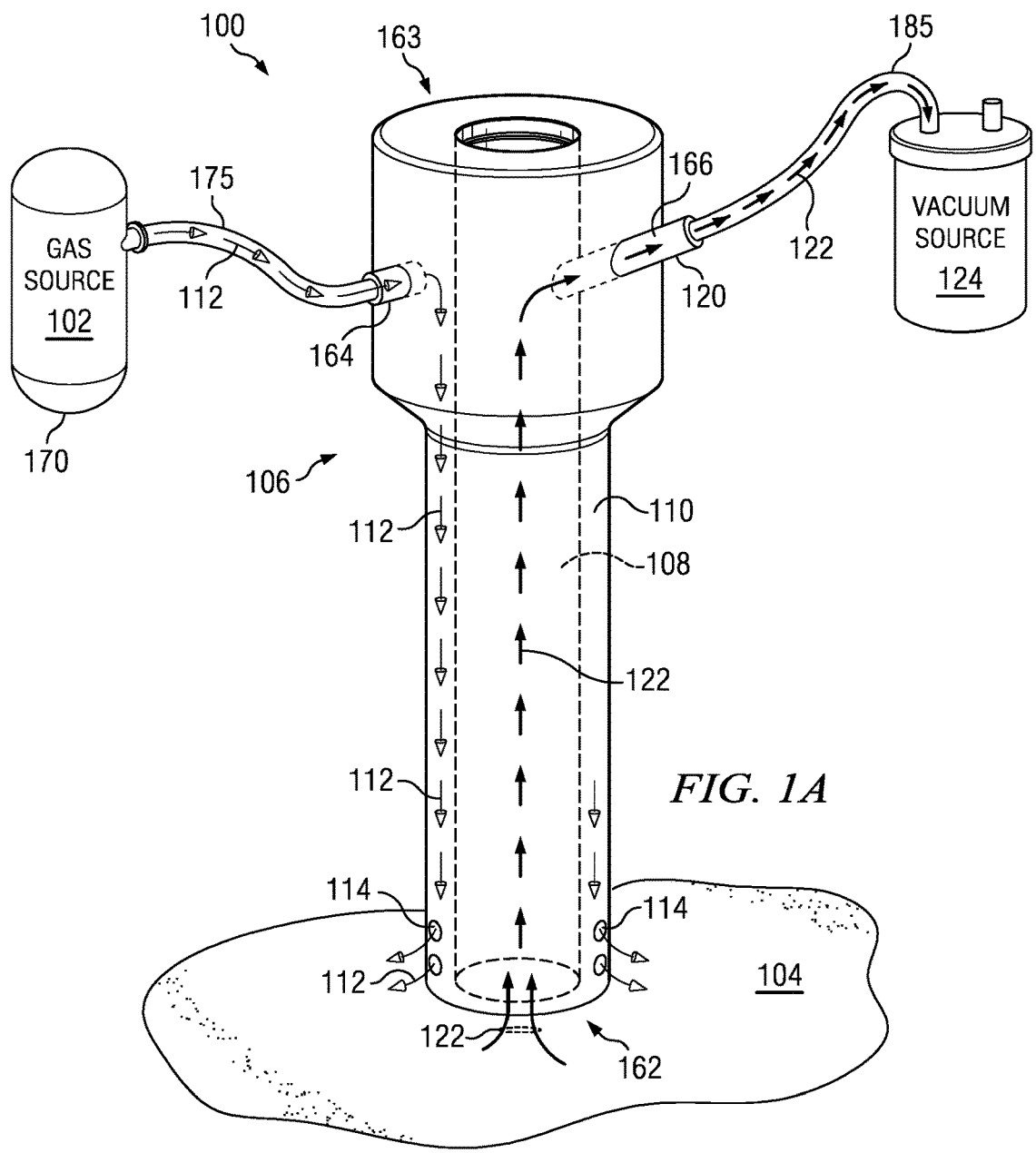
FIG. 1B
FIG. 1A

METHOD AND SYSTEM FOR GAS MAINTENANCE TO A BODY CAVITY USING A TROCAR

CROSS REFERENCE

This application is a continuation application of U.S. application Ser. No. 16/271,072, filed Feb. 8, 2019, and entitled "Method and System for Gas Maintenance to a Body Cavity Using a Trocar," which is a continuation-in-part application of U.S. application Ser. No. 14/792,873, filed Jul. 7, 2015, and entitled "Method and System for Gas Maintenance to a Body Cavity Using a Trocar," now U.S. Pat. No. 10,238,421 issued Mar. 26, 2019. The contents of each of the applications to which priority is claimed are incorporated herein by reference in their entirety.

TECHNICAL FIELD

The present disclosure relates generally to medical procedures and more particularly to a method and system for gas maintenance to a body cavity using a trocar.

BACKGROUND

Laparoscopic surgery is a standard procedure in hospitals. Abdominal and chest cavity operations are being performed with instruments inserted through small incisions into interior portions of the body. Such laparoscopic procedures are now considered the treatment of choice for operations such as the removal of the gall bladder, spleen, adrenal glands, uterus, and ovaries. These laparoscopic procedures are accomplished via access through a device typically known as a trocar. A trocar facilitates the introduction of laparoscopic instruments into the abdomen or chest of the body. These instruments are typically introduced into regions under fluid pressure. This fluid may be a gas, referred to herein as an insufflation gas.

Providing an insufflation gas into a body cavity is referred to as insufflation. Currently, insufflation is performed by providing a regulated pressurized insufflation gas to the peritoneal cavity via a cannula of the trocar. This insufflation gas, typically carbon dioxide, is supplied to a connection on the trocar tube by a flexible hose attached thereto. The medical instrument going through the innermost tube of the trocar, should be sealed relative to the trocar so the insufflation gas will not escape from the patient.

A physician can use a trocar device to introduce different types of instruments into a patient. In order to reduce incisions into the body, typically the insufflation gas is delivered into a body cavity during specific medical procedures or treatment is done via a trocar that also allows insertion of an instrument via the innermost tube of the trocar. The purpose of using such a device is to inflate or distend the body cavity to (1) allow the surgeon to explore the area in which the surgery will be performed and (2) provide a view of the site to be treated or observed.

Insufflation is used in many common procedures including endoscopic surgical procedures, laparoscopic procedures performed on the abdominal cavity and orthoscopic procedures performed on the chest cavity. Additional trocars can be used during the same surgical procedure to remove surgical smoke from the patient cavity or to continuously measure pressure within the body cavity. These trocars typically also allow for the insertion of an instrument via the innermost tube of the trocar.

Examples of one or more trocars are provided in U.S. Pat. No. 8,715,219 (the '219 Patent), U.S. Pat. No. 7,285,112 (the '112 Patent), and U.S. Pat. No. 8,216,189 (the '189 Patent), which are hereby incorporated by reference as if fully set forth herein.

SUMMARY

According to one embodiment, a trocar assembly having a proximal end and a distal end comprises an inner tubular member and an outer tubular member. The inner tubular member is formed with an opening at the proximal end and an opening at the distal end, the openings adapted to provide access for one or more surgical instruments during a surgical procedure. The outer tubular member is disposed about the inner tubular member, the outer tubular member being partitioned into at least a first chamber and a second chamber, wherein: the inner tubular member is separated from the outer tubular member by an inner wall; the first chamber is separated from the second chamber; and the first chamber and the second chamber are defined by the inner wall and an outer wall of the outer tubular member.

According to another embodiment, a method includes positioning a distal portion of a trocar into a patient cavity, the trocar comprising an outer tubular member disposed about an inner tubular member, the outer tubular member being partitioned into at least a first chamber and a second chamber, wherein: the inner tubular member is separated from the outer tubular member by an inner wall; the first chamber is separated from the second chamber; and the first chamber and the second chamber are defined by the inner wall and an outer wall of the outer tubular member. The method further includes inserting a surgical instrument into the inner tubular member and supplying an insufflation gas to the patient cavity through the first chamber of the outer tubular member, wherein the insufflation gas is directed to the patient cavity through one or more apertures positioned in the outer wall that partially defines the first chamber.

The teachings of the disclosure provide one or more technical advantages. Embodiments of the disclosure may have none, some, or all of these advantages. For example, in some embodiments, a method and apparatus for supplying insufflation fluid to a patient cavity is provided that allow for measurement of patient cavity pressure and/or removal of smoke from with the patient cavity. This alleviates concerns associated with using multiple trocars at the same time. Other advantages will be apparent to those of skill in the art.

BRIEF DESCRIPTION OF THE DRAWINGS

For a more complete understanding of embodiments of the disclosure and the potential advantages thereof, reference is now made to the following written description taken in conjunction with the accompanying drawings, in which:

FIGS. 1A and 1B illustrate one embodiment of a system to supply an insufflation gas to a patient cavity that uses a trocar having an inner lumen and an outer lumen in which the outer lumen allows for the insufflation gas to be delivered to the patient cavity and the inner lumen provides a path for smoke to be removed from the patient cavity;

DETAILED DESCRIPTION OF THE DRAWINGS

Figure 2B:
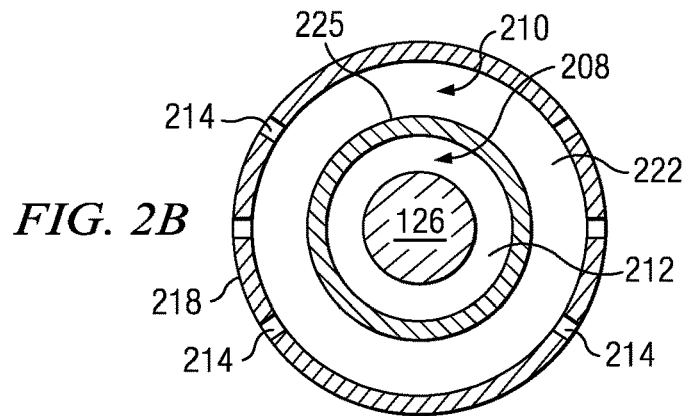
FIGS. 2A and 2B illustrate one embodiment of a system to supply an insufflation gas to a patient cavity that uses a trocar having an inner lumen and an outer lumen in which the inner lumen allows for the insufflation gas to be delivered to the patient cavity and the outer lumen provides a path for smoke to be removed from the patient cavity.

The teachings of the present disclosure recognize that using multiple trocars for gas delivery, smoke removal and pressure sensing at once can be undesirable in some instances. For example, improper placement of a trocar with gas delivery and a trocar with smoke removal could lead to direct channeling of the newly delivered gas into the smoke removal trocar. This direct channeling of new gas could severely limit the amount of smoke removal from the patient cavity. The present disclosure addresses problems associated with using multiple trocars for gas delivery, smoke removal and pressure sensing by providing methods and systems that allow removal of smoke and/or pressure measurements while also providing a path from an insufflation gas to a patient cavity using a single trocar. Example embodiments of the invention are best understood by referring to FIGS. 1A through 7B of the drawings and the description below, like numerals being used for like and corresponding parts of the various drawings.

FIGS. 1A and 1B illustrate one embodiment of a system 100 to supply an insufflation gas 102 to a patient cavity 104 that uses a trocar having an inner lumen and an outer lumen in which the outer lumen allows for the insufflation gas to be delivered to the patient cavity and the inner lumen provides a path for smoke to be removed from the patient cavity.

System 100 includes a trocar 106, an insufflation gas source 170, a vacuum source 180, a conduit 175 for supplying insufflation gas 102 to a portion of trocar 106, and a conduit 185 for applying a vacuum from vacuum source 124 to a portion of trocar 106. A distal end 162 of trocar 106 is inserted into patient cavity 104 while the proximal end 164 allows an instrument 126 to be inserted such that trocar 106 provides access to body cavity 104 for the instruments 126. Suitable seals may be positioned in or around trocar 106 for preventing or reducing leakage of fluid out of trocar 106. Patient cavity 104 may be accessed through an incision made with an obturator, which may be included in the same kit or package with trocars described herein.

Trocar 106 is formed with an inner lumen 108 and an outer lumen 110. Inner lumen 108 is separated from outer lumen 110 by an inner wall 125. Outer lumen 110 is surrounded by an outer wall 118. Outer wall 118 may be formed with one or more holes or apertures 114 near a distal end 162 of trocar 106. A surgical instrument 126 may be positioned within inner lumen 108 to allow access to patient cavity 104 by a surgeon using surgical instrument 126. An open gas tubing connection 120 couples inner lumen 108 to conduit 185. Open gas tubing connection 120 may include a vacuum break 166. Tubing 175 couples insufflation fluid source 170 to outer lumen 110 by connection 164.

In operation, insufflation gas 102 is delivered to patient cavity 104 from insufflation gas source 170 through conduit 175 and outer lumen 110, as indicated by arrows 112. Insufflation gas 102 enters patient cavity 104 via apertures 114 in outer wall 118 of the trocar 106.

Smoke is sometimes present in patient cavity 104 due to electrocautery and other techniques (e.g. harmonic scalpels), and it is often desirable to remove such smoke from patient cavity 104. The teachings of the disclosure recognize deficiencies associated with using a second trocar for smoke removal in addition to the trocar used to provide insufflation gas to the patient.

Surgical instruments 126 may be affected by electromagnetic frequencies emanating from objects in the operating room. Accordingly, this disclosure recognizes wrapping or shielding surgical instruments 126, cables associated with such instruments 126, and/or cables otherwise coupled to or associated with trocar 106 to protect against incoming emissions of electromagnetic frequencies. In some embodiments, shielding surgical instruments 126 or cables comprises surrounding surgical instruments 126 or cables with conductive or magnetic materials.

Inner lumen 108 of trocar 106 allows for smoke in patient cavity 104 to be removed using the same trocar 106 as is used for supplying insufflation gas 102 to patient cavity 104. Smoke is removed through inner lumen 108 via connection 120, which couples inner lumen 108 to conduit 185, as indicated by arrows 122. The smoke from patient cavity 104 enters inner lumen 108 through an opening at distal end 162 of trocar 106. The smoke can be vented into the operating room, filtered into the operating room, or vented out of the operating room via a vacuum source 124. Inner lumen 108 also allows for insertion of a surgical instrument 126 at the same time as smoke is being removed.

Thus, trocar 106 allows for supplying insufflation gas 102 to a patient cavity 104 and removing smoke from the patient cavity 104 without the use of multiple trocars 106. Additional embodiments of systems and methods that allow supplying insufflation gas 102 to patient cavity 104 along with cavity pressure measurement and/or smoke removal are described below in conjunction with FIGS. 2A through 7B. Additional details of certain portions of the described systems and methods are provided after the description of FIG. 7B.

Figure 2A:
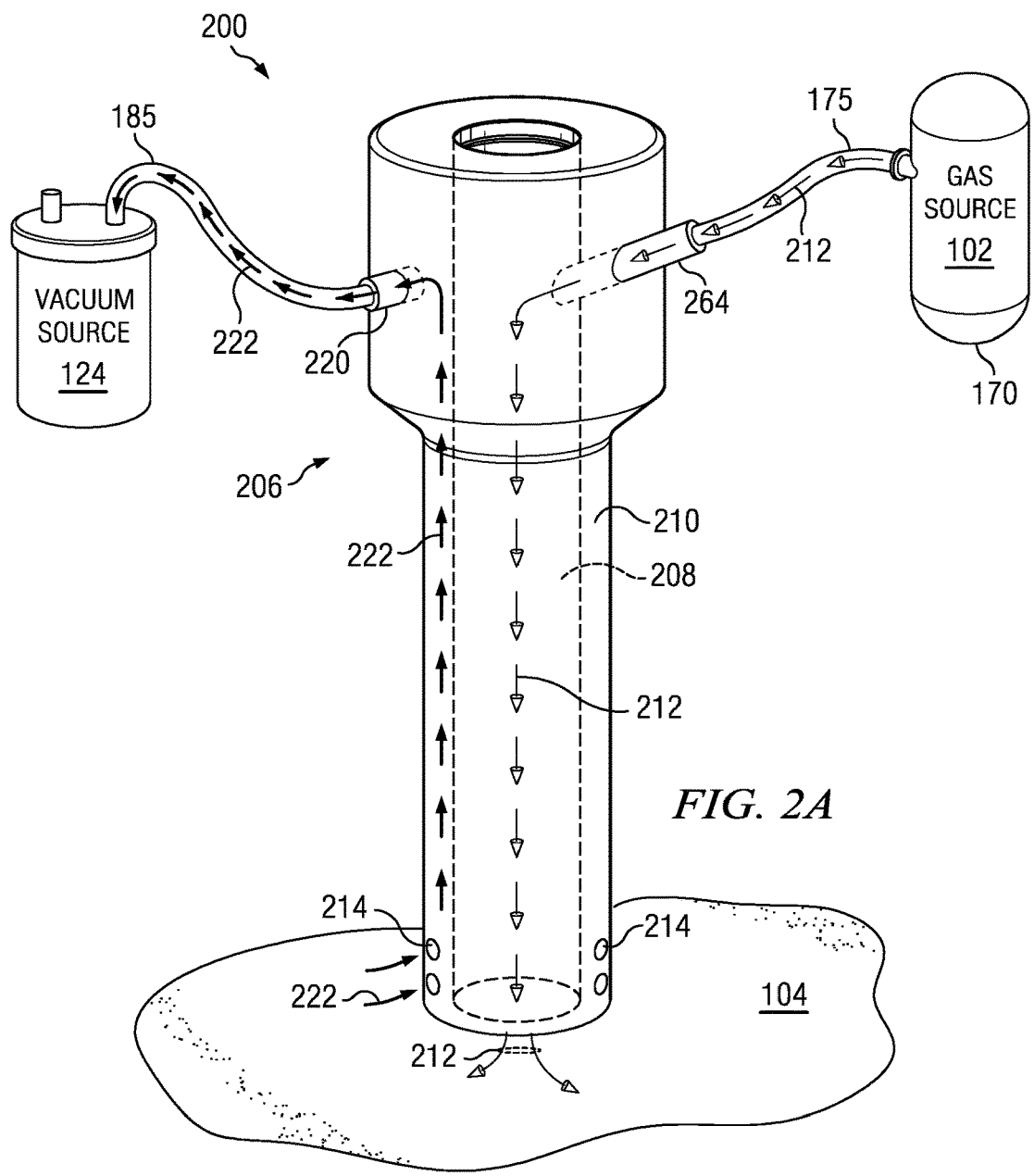

FIGS. 2A and 2B illustrate one embodiment of a system 200 to supply an insufflation gas 102 to a patient cavity 104 that uses a trocar having an inner lumen and an outer lumen in which the inner lumen allows for the insufflation gas to be delivered to the patient cavity and the outer lumen provides a path for smoke to be removed from the patient cavity.

System 200 includes a trocar 206 having an inner lumen 208 and an outer lumen 210. Trocar 206 is analogous to trocar 106, with analogous portions having analogous reference numerals (e.g., inner wall 225 is analogous to inner wall 125). System 200 is analogous to system 100, except that insufflation gas 102 is supplied to patient cavity 104 via inner lumen 208, rather than outer lumen 110 as in system 100, and smoke is removed from patient cavity 104 via outer lumen 210 rather than inner lumen 108 as in system 100. As such, system 200 includes an open gas tubing connection 220 between conduit 185 and outer lumen. Connection 220 is adapted to connect conduit 185 to outer lumen 210. And system 200 includes a connection 264 between conduit 175 and inner lumen 208 adapted to connect conduit 175 to inner lumen 208.

In operation, insufflation gas 102 is delivered to patient cavity 104 from insufflation gas source 170 through conduit 175 and inner lumen 208, as indicated by arrows 212. Insufflation gas 102 enters patient cavity 104 via an opening at distal end 262 of trocar 206. Inner lumen 208 also allows for the insertion surgical instrument 126 at the same time as insufflation gas 102 is being delivered.

Outer lumen 210 of trocar 206 allows for smoke in patient cavity 104 to be removed using the same trocar 206 as is used for supplying insufflation gas 102 to patient cavity 104. Smoke is removed through outer lumen inner 210 via connection 220, which couples outer lumen 210 to conduit 185, as indicated by arrows 222. The smoke from patient cavity 104 enters outer lumen 210 through apertures 214 in an outer wall 218 of trocar 206. The smoke can be vented into the operating room, filtered into the operating room, or vented out of the operating room via a vacuum source 124.

Figure 3B:
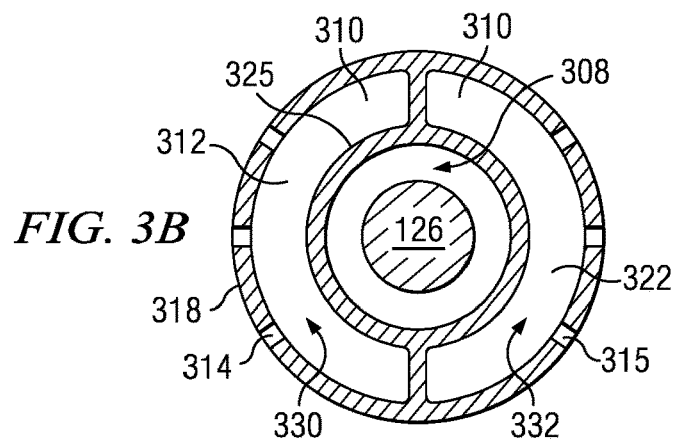
FIGS. 3A and 3B illustrate one embodiment of a system to supply an insufflation gas to a patient cavity that uses a trocar having an inner lumen and an outer lumen with a plurality of chambers in which one of the chambers in the outer lumen allows for the insufflation gas to be delivered to the patient cavity and the other chamber in the outer lumen provides a path for smoke to be removed from the patient cavity.
Figure 3A:
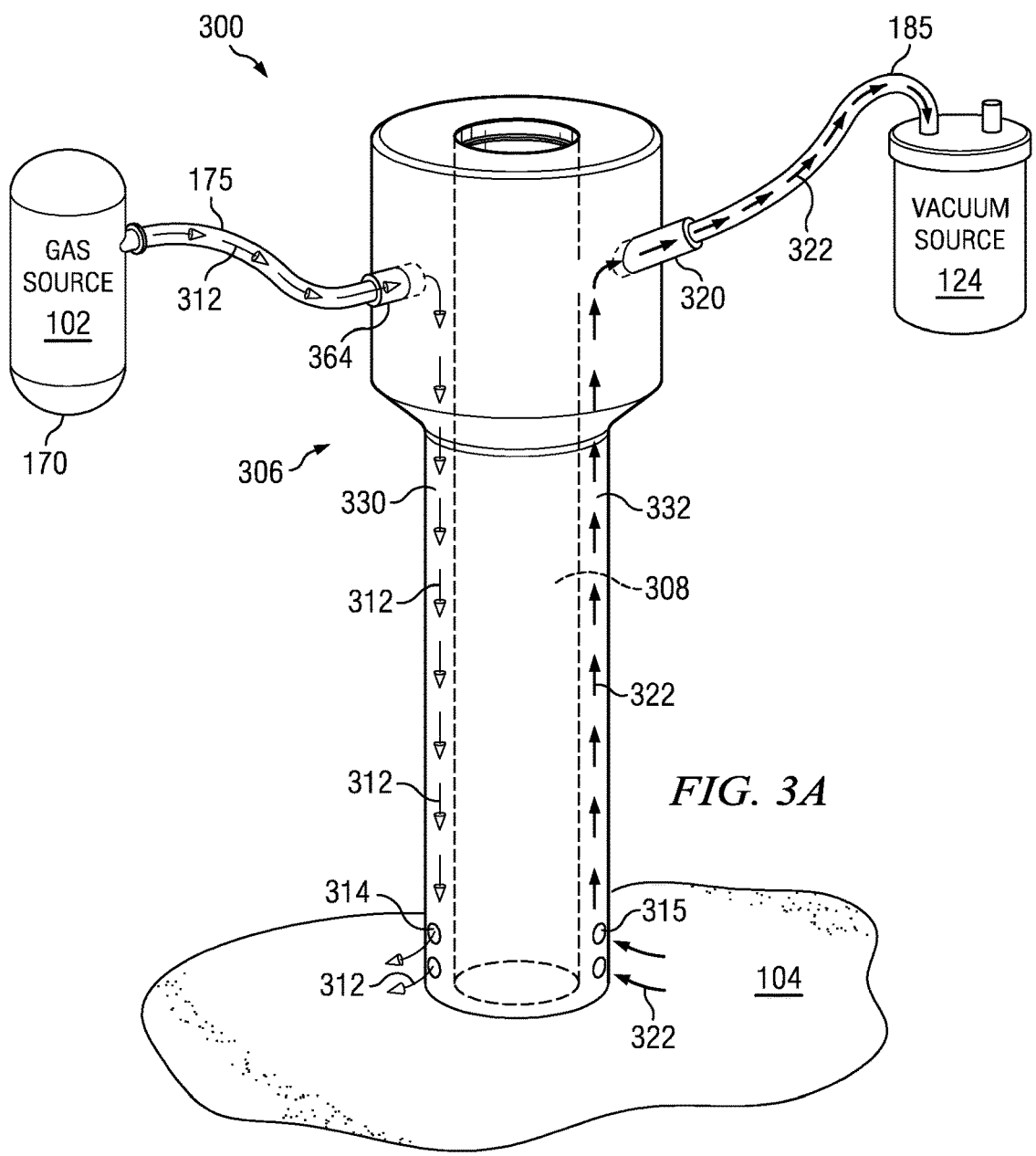

FIGS. 3A and 3B illustrate one embodiment of a system 300 to supply an insufflation gas 102 to a patient cavity 104 that uses a trocar having an inner lumen and an outer lumen with a plurality of chambers in which one of the chambers in the outer lumen allows for the insufflation gas to be delivered to the patient cavity and the other chamber in the outer lumen provides a path for smoke to be removed from the patient cavity.

System 300 includes a trocar 306. Trocar 306 is analogous to trocar 106, with analogous portions having analogous reference numerals, except that trocar 306 is formed with an inner lumen 308 and an outer lumen 310 having a plurality of chambers 330, 332. Outer wall 318 is formed with one or more holes or apertures 314 near a distal end 362 of trocar 306 that are associated with chamber 330. Outer wall 118 may also be formed with one or more holes or apertures 315 proximate distal end 362 of trocar 306 that are associated with chamber 332. System 300 is analogous to system 100, with analogous portions having analogous reference numerals, except that system 300 includes an open gas tubing connection 320 adapted to connect to chamber 332 of outer lumen 310 to conduit 185. And, system 300 includes a connection 364 adapted to connect conduit 312 to chamber 330 of outer lumen 310.

In operation, insufflation gas 102 is delivered to patient cavity 104 from insufflation gas source 170 through conduit 175 and chamber 330 of outer lumen 310, as indicated by arrows 312. Insufflation gas 102 enters patient cavity 104 via apertures 314 in an outer wall 318 of the trocar 106.

The other chamber in outer lumen 310, chamber 332, allows for smoke in patient cavity 104 to be removed using the same trocar 306 as is used for supplying insufflation gas 102 to patient cavity 104. Smoke is removed through chamber 332 of outer lumen 310 via connection 320, which couples chamber 332 of outer lumen 308 to conduit 185, as indicated by arrows 322. The smoke from patient cavity 104 enters chamber 332 of outer lumen 108 through apertures 315 in outer wall 318 of trocar 306. The smoke can be vented into the operating room, filtered into the operating room, or vented out of the operating room via a vacuum source 124.

Inner lumen 308 allows for insertion of surgical instrument 126 at the same time as smoke is being removed and/or at the same time insufflation gas is being supplied to patient cavity 104.

Figure 4B:
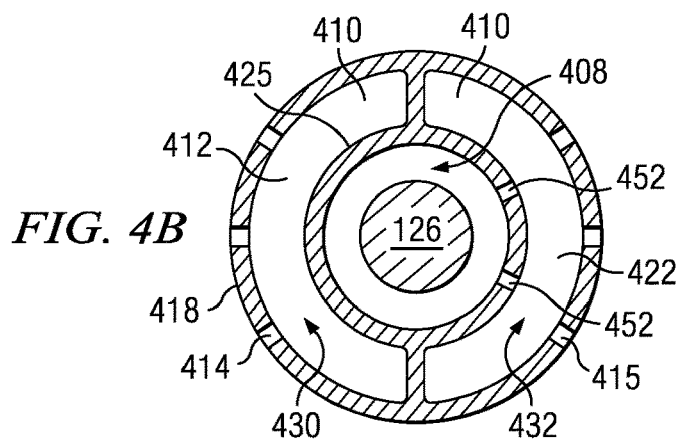
FIGS. 4A and 4B illustrate one embodiment of a system to supply an insufflation gas to a patient cavity that uses a trocar having an inner lumen and an outer lumen with a plurality of chambers in which one of the chambers in the outer lumen allows for the insufflation gas to be delivered to the patient cavity and the other chamber in the outer lumen allows pressure measurement of the patient cavity.
Figure 4A:
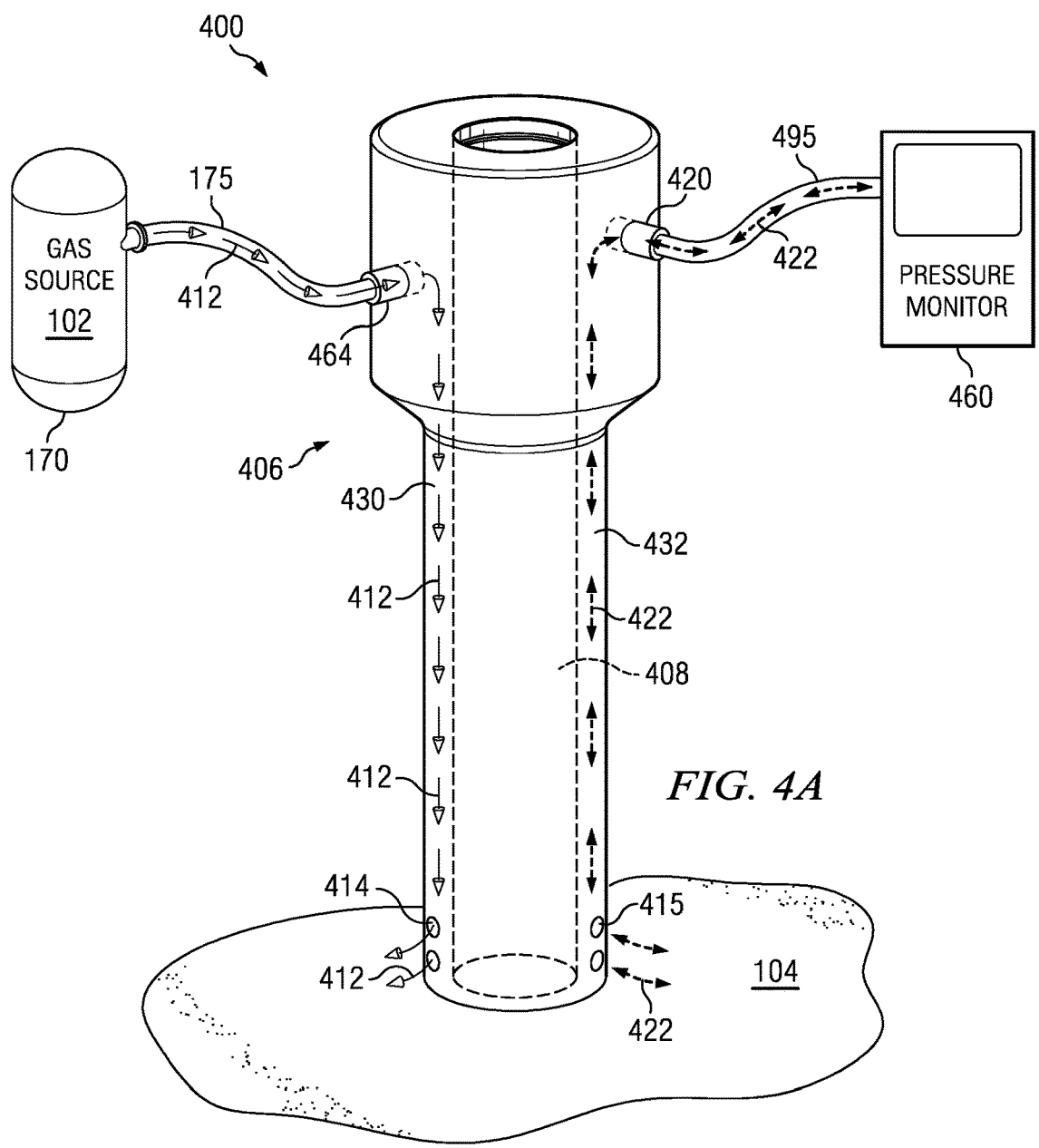

FIGS. 4A and 4B illustrate one embodiment of a system 400 to supply an insufflation gas 102 to a patient cavity 104 that uses a trocar having an inner lumen and an outer lumen with a plurality of chambers in which one of the chambers in the outer lumen allows for the insufflation gas to be delivered to the patient cavity and the outer chamber in the outer lumen allows pressure measurement of the patient cavity.

System 400 is analogous to system 300, except that chamber 432 of outer lumen 410 is used to effect pressure measurement of patient cavity 104, as opposed to chamber 332 being used to remove smoke from patient cavity 104. As such system 400 includes a monitor 460 for measuring pressure that is connected to trocar 406 by a suitable conduit 495 for such a pressure measurement. Connection 420 couples conduit 495 to inner lumen chamber 432. Trocar 406 is analogous to trocar 306, with analogous portions having analogous reference numerals. Connection 464 may be adapted to couple outer chamber 432 to conduit 185.

In operation, insufflation gas 102 is delivered to patient cavity 104 from insufflation gas source 170 through conduit 175 and chamber 430 of outer lumen 410, as indicated by arrows 412. Insufflation gas 102 enters patient cavity 104 via apertures 414 in an outer wall 418 of the trocar 406.

The other outer lumen chamber, chamber 432, allows for pressure measurement by creating a direct connection from patient cavity 104 through apertures 415 to a monitor 460 external to the patient, as illustrated by bi-directional arrows 450. The direct connection has a minimal pressure drop to ensure accurate measurement. Outer lumen 410 may or may not be connected to inner lumen 408 via one or more holes 452 in inner wall 425.

Figure 5B:
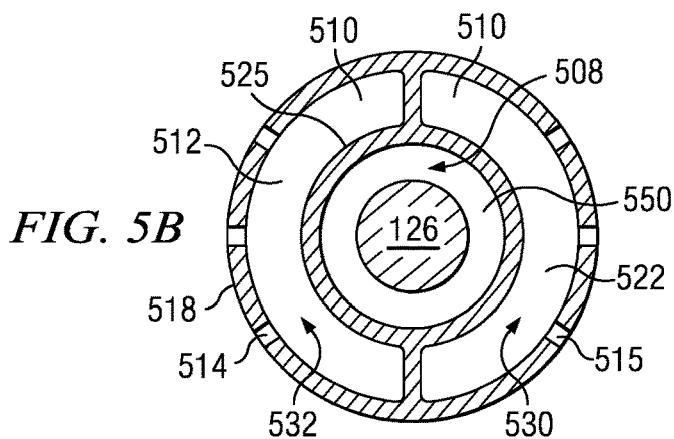
FIGS. 5A and 5B illustrate one embodiment of a system to supply an insufflation gas to a patient cavity that uses a trocar having an inner lumen and an outer lumen with a plurality of chambers in which one of the chambers in the outer lumen allows for the insufflation gas to be delivered to the patient cavity, the other chamber in the outer lumen provides a path for smoke to be removed from the patient cavity, and the inner lumen allows pressure measurement of the patient cavity.
Figure 5A:
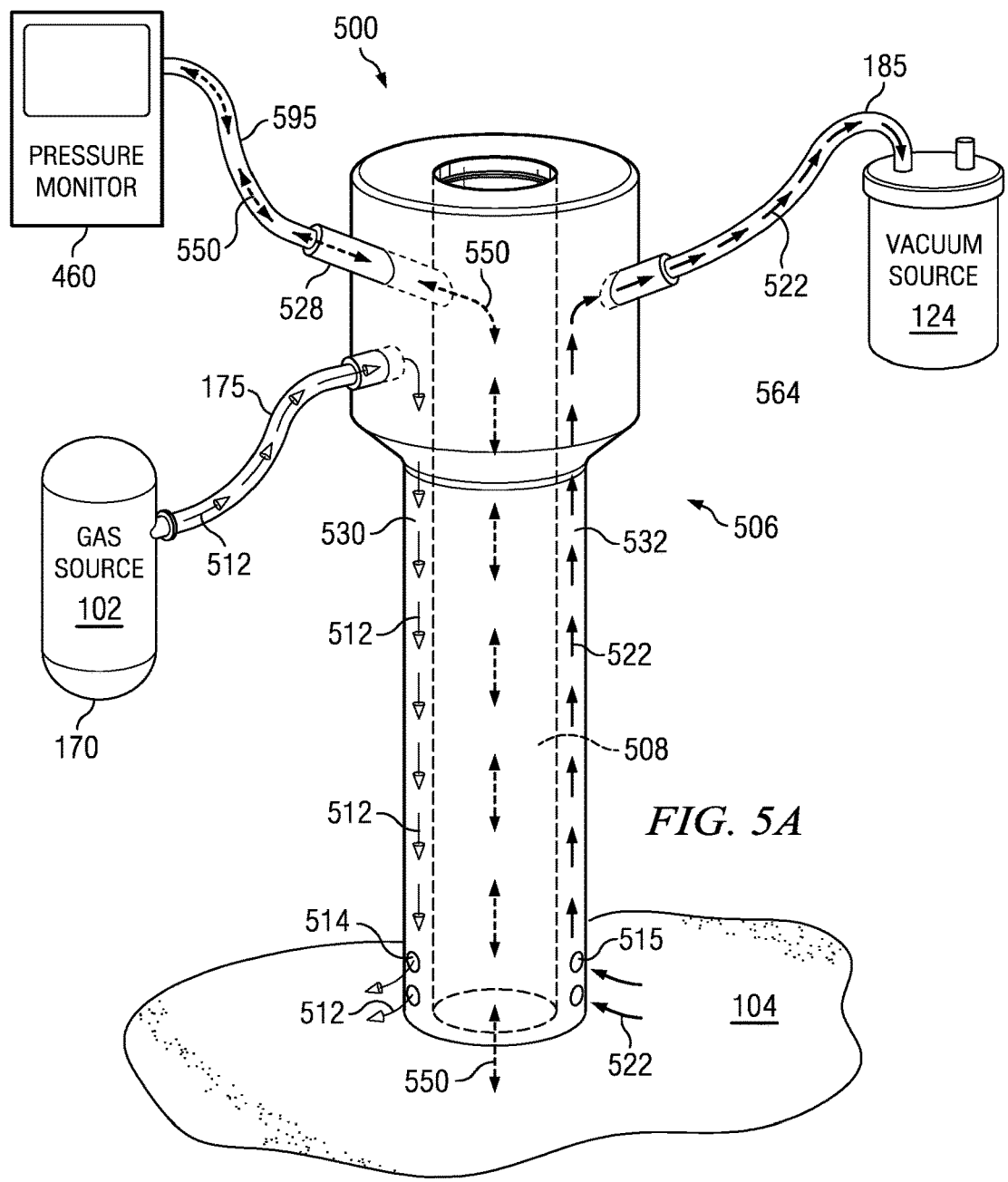

FIGS. 5A and 5B illustrate one embodiment of a system 500 to supply an insufflation gas 102 to a patient cavity 104 that uses a trocar having an inner lumen and an outer lumen with a plurality of chambers in which one of the chambers in the outer lumen allows for the insufflation gas to be delivered to the patient cavity, the other chamber in the outer lumen provides a path for smoke to be removed from the patient cavity, and the inner lumen allows pressure measurement of the patient cavity.

System 500 includes trocar 506, which is analogous to trocar 306, with analogous portions having analogous reference numerals. System 500 is analogous to system 300 except for the addition of pressure measurement system 460 coupled by a conduit 595 and connection 598 to inner lumen 508 of trocar 506. Connection 598 may be any suitable connection for coupling inner lumen 508 to conduit 595.

In operation, system 500 performs similarly to system 300. In particular, insufflation gas 102 is delivered to patient cavity 104 from insufflation gas source 170 through conduit 175 and chamber 530 of outer lumen 510, as indicated by arrows 512. Insufflation gas 102 enters patient cavity 104 via apertures 514 in an outer wall 518 of the trocar 506.

The other chamber in outer lumen 510, chamber 532, allows for smoke in patient cavity 104 to be removed using the same trocar 506 as is used for supplying insufflation gas 102 to patient cavity 104. Smoke is removed from patient cavity 104 through apertures 515 through chamber 532 of outer lumen 510 via connection 520, which couples chamber 532 of outer lumen 508 to conduit 585, as indicated by arrows 522. The smoke from patient cavity 104 enters chamber 532 of outer lumen 108 through aperture 515 in outer wall 518 of trocar 506. The smoke can be vented into the operating room, filtered into the operating room, or vented out of the operating room via a vacuum source 124.

In addition, inner lumen chamber 508 allows for pressure measurement by creating a direct connection from patient cavity 104 to a monitor 460 external to the patient, as indicated by bi-directional arrows 550. The direct connection has a minimal pressure drop to ensure accurate measurement.

Figure 6B:
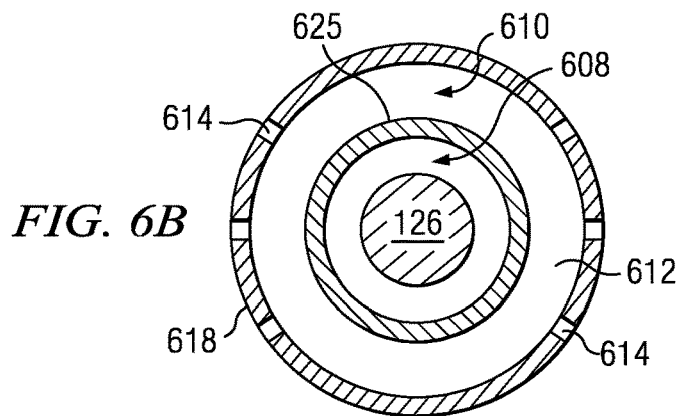
FIGS. 6A and 6B illustrate one embodiment of a system to supply an insufflation gas to a patient cavity that uses a trocar having an inner lumen and an outer lumen in which the outer lumen allows for the insufflation gas to be delivered to the patient cavity and the inner lumen allows pressure measurement of the patient cavity.
Figure 6A:
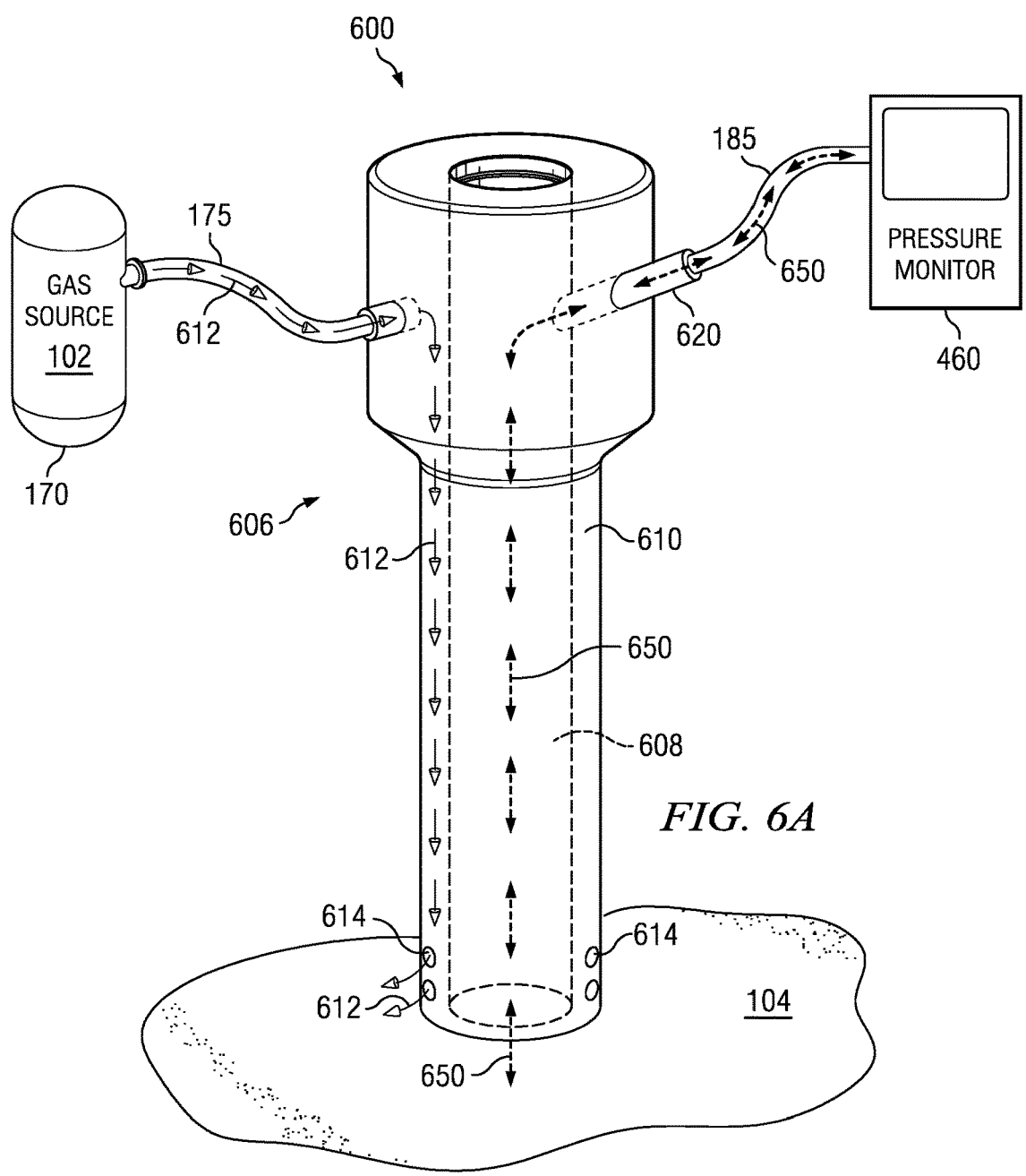

FIGS. 6A and 6B illustrate one embodiment of a system 600 to supply an insufflation gas 102 to a patient cavity 104 that uses a trocar having an inner lumen and an outer lumen in which the outer lumen allows for the insufflation gas to be delivered to the patient cavity and the inner lumen allows pressure measurement of the patient cavity.

System 500 includes trocar 506, which is analogous to trocar 106, with analogous portions having analogous reference numerals. System 600 is analogous to system 100, with analogous portions having analogous reference numerals, except that system 600 includes monitor 460 for measuring pressure. System 600 also includes a suitable connection 620 for such pressure measurement that couples inner lumen 608 of trocar 606 to conduit 185.

In operation, insufflation gas 102 is delivered to patient cavity 104 from insufflation gas source 170 through conduit 175 and outer lumen 610, as indicated by arrows 612. Insufflation gas 102 enters patient cavity 104 via apertures 614 in outer wall 618 of the trocar 606.

Inner lumen 608 allows for pressure measurement by creating a direct connection from patient cavity 104 to a monitor 460 external to the patient, as indicated by bi-directional arrows 650. The direct connection has a minimal pressure drop to ensure accurate measurement.

Figure 7B:
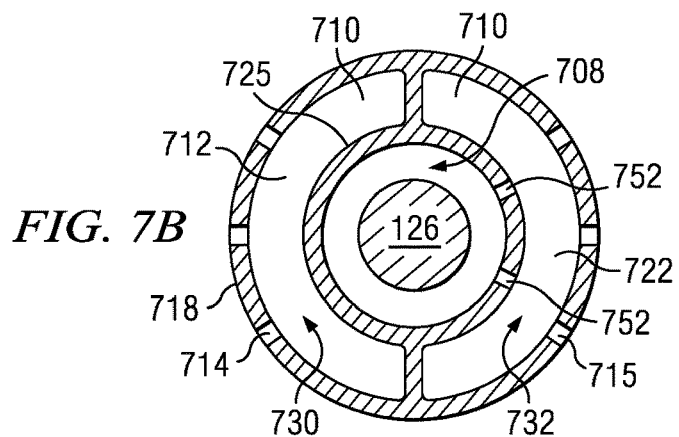
FIGS. 7A and 7B illustrate one embodiment of a system to supply an insufflation gas to a patient cavity that uses a trocar having an inner lumen and an outer lumen with a plurality of chambers in which one of the chambers in the outer lumen allows for the insufflation gas to be delivered to the patient cavity, the other chamber in the outer lumen allows pressure measurement of the patient cavity, and the inner lumen provides a path for smoke to be removed from the patient cavity.
Figure 7A:
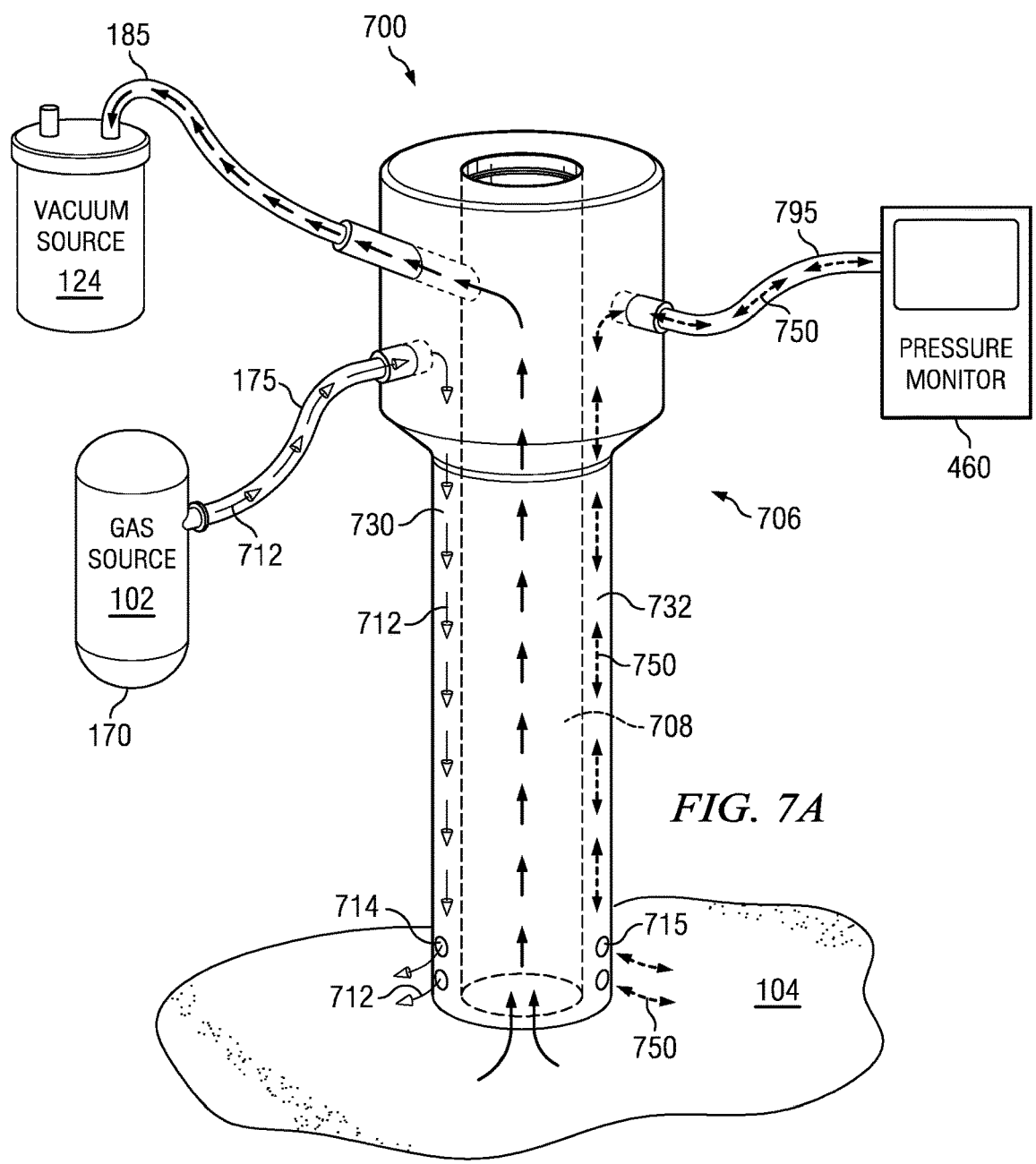

FIGS. 7A and 7B illustrate one embodiment of a system to supply an insufflation gas to a patient cavity that uses a trocar having an inner lumen and an outer lumen with a plurality of chambers in which one of the chambers in the outer lumen allows for the insufflation gas to be delivered to the patient cavity, the other chamber in the outer lumen allows pressure measurement of the patient cavity, and the inner lumen provides a path for smoke to be removed from the patient cavity.

System 700 includes trocar 706, which is analogous to trocar 506, with analogous portions having analogous reference numerals. System 700 is analogous to the system 500 except that pressure measurement occurs through outer chamber 732 of trocar 700 as opposed to through inner lumen 508 of system 500, and smoke is removed from patient cavity 104 through inner lumen 708 of trocar 700 as opposed to through outer chamber 552 of system 500. A connector 721 couples conduit 185 to inner lumen 730.

In operation, insufflation gas 102 is delivered to patient cavity 104 from insufflation gas source 170 through conduit 175 and chamber 730 of outer lumen 710, as indicated by arrows 712. Insufflation gas 102 enters patient cavity 104 via apertures 714 in an outer wall 718 of the trocar 706.

The other outer lumen chamber, chamber 732, allows for pressure measurement by creating a direct connection from patient cavity 104 to a monitor 460 external to the patient, as illustrated by bi-directional arrows 750. The direct connection has a minimal pressure drop to ensure accurate measurement. Outer lumen 710 may or may not be connected to inner lumen 708 via one or more holes 752 in inner wall 725.

Inner lumen 708 allows for smoke to be removed via an open gas tubing connection 721 to inner lumen 708. The smoke can be vented into the operating room, filtered into the operating room, or vented out of the operating room via vacuum source 124. Inner lumen 708 also allows for the insertion of a surgical instrument 126 at the same time as smoke is being removed.

Thus, the systems of FIG. 1A through 7B allow removal of smoke and/or pressure measurements while also providing a path from an insufflation gas to a patient cavity using a single trocar. In some embodiments this avoids the use of multiple trocars in a patient at the same time; however, the teachings of the present disclosure recognize that the described systems and methods may be used in conjunction with the use of multiple trocars if desired.

Figure 8B:
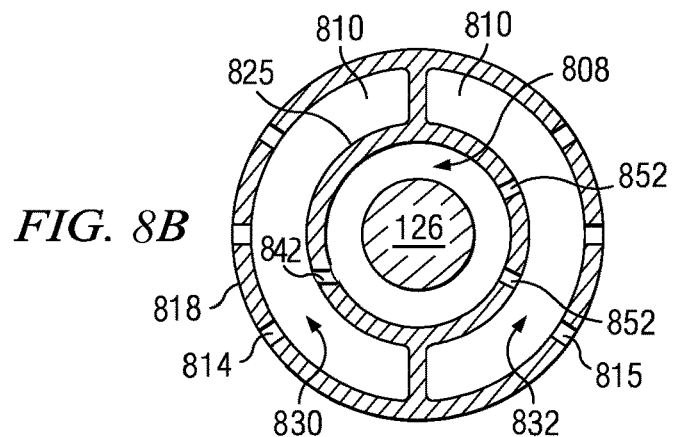
FIGS. 8A and 8B illustrate one embodiment of a system to supply an insufflation gas to a patient cavity that uses a trocar having an inner lumen, an outer lumen partitioned into a plurality of chambers, and a plurality of apertures, wherein the plurality of apertures provide an alternative pathway for taking a pressure measurement.
Figure 8A:
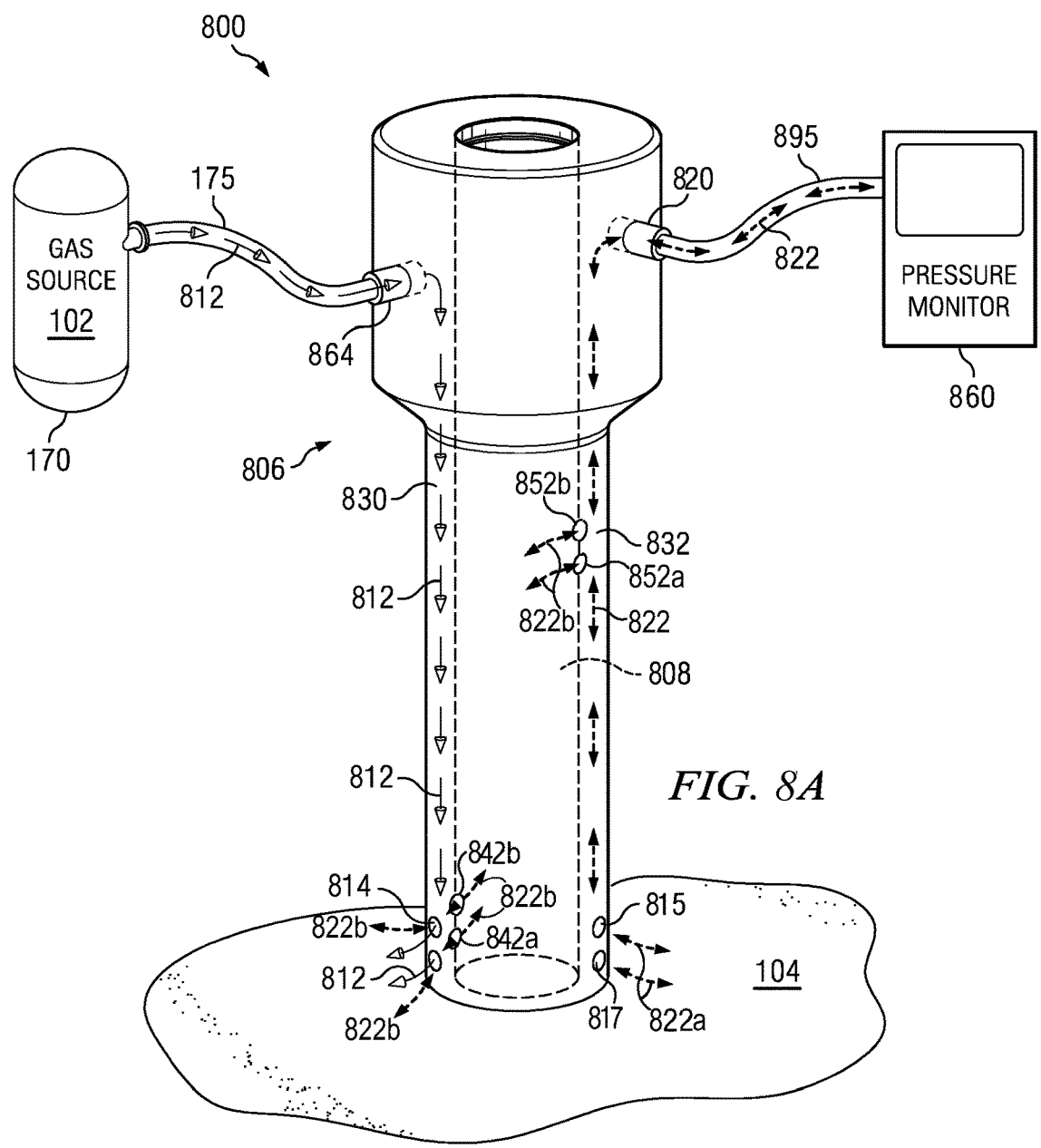

FIGS. 8A and 8B illustrate one embodiment of a system 400 to supply an insufflation gas 102 to a patient cavity 104 that uses a trocar 806 having an inner lumen 808 and an outer lumen 810 with a plurality of chambers (i.e., a first chamber 830 and a second chamber 832). As depicted in FIG. 8A, one of the chambers in the outer lumen 810 allows for the insufflation gas to be delivered to the patient cavity (i.e., chamber 830 and the other chamber in the outer lumen 810 allows pressure measurement of the patient cavity (i.e., chamber 832).

System 800 is analogous to system 400 except that trocar 806 provides a secondary pathway for measuring pressure. In view of the similarities, analogous portions are identified using analogous reference numerals. As depicted in FIG. 8A, a pressure of patient cavity 104 may be measured through a chamber 832 via a first pathway 822a or a second pathway 822b. This disclosure recognizes certain benefits of providing a secondary pathway (e.g., pathway 822b). For example, a secondary pathway (e.g., pathway 822b) may permit pressure measurements to be taken when pressure measurements cannot be taken via first pathway 822a. This may occur, for example, when tissue and/or a surgical tool 126 in patient cavity 104 is blocking one or more apertures positioned in outer wall 818 of chamber 832 (e.g., apertures 815 and 817). In such case, a pressure measurement may be taken via second pathway 822b. This is beneficial because, without an alternative pathway permitting pressure feedback information, insufflation gas 102 may buildup in patient cavity 104.

In some embodiments, second pathway 822b comprises one or more apertures permitting fluid to pass through chamber 830 and inner lumen 808 into chamber 832. As depicted in FIG. 8A, second pathway 822b comprises aperture 814 located in outer wall 810 within chamber 830, apertures 842a, 842b located in inner wall 825 within chamber 830, and apertures 852a, 852b located in inner wall 825 within chamber 832. Like first pathway 822a, second pathway 822b may continue through a connection 820 and conduit 895 and terminate at monitor 860.

In operation, insufflation gas 102 is delivered to patient cavity 104 from insufflation gas source 170 through conduit 175 and connection 864 into chamber 830 of outer lumen 810, as indicated by arrows 812. Insufflation gas 102 enters patient cavity 104 via apertures 814 in an outer wall 818 of the trocar 806. The other outer lumen chamber, chamber 832, allows for pressure measurement. As described above, chamber 832 may include one or more pathways allowing for pressure measurement. A first pathway creates a connection from patient cavity 104 through apertures 815, 817 (as illustrated by bi-directional arrows 822a) to chamber 832 (as illustrated by bi-directional arrows 822) and further to monitor 860 (as illustrated by bi-directional arrows 822). First pathway has a minimal pressure drop to ensure accurate measurement. A second pathway creates a connection from patient cavity 104 through apertures 814, 842, and 852 (as illustrated by bi-directional arrows 822b) to chamber 832 (as illustrated by bi-directional arrows 822) to and further to monitor 860 (as illustrated by bi-directional arrows 822).

Although this disclosure describes and depicts second pathway 822b as an alternative pathway for measuring pressure of patient cavity 104, this disclosure recognizes that second pathway 822b may also be utilized as a pathway for removing smoke and/or providing insufflation gas when one or more other apertures of a trocar are blocked. This disclosure also recognizes other alternative pathways. For example, this disclosure recognizes a third pathway comprising apertures in outer wall 818 within chamber 830 (e.g., aperture 814) and in inner wall 825 within chamber 830 (e.g., aperture 842) for permitting fluid to flow into inner lumen 808 when the opening at the distal end of inner lumen 808 is blocked. Such pathway may further comprise a connection extending through inner wall 825 and outer wall 818 (see e.g., connection 528 of FIG. 5A) coupled to a conduit which is in turn coupled to a monitor 860, a gas source 170, and/or a vacuum source 124. As another example, this disclosure recognizes a fourth pathway comprising one or more apertures in outer wall 818 within chamber 832 (e.g., apertures 815, 817) and in inner wall 825 within chamber 832 (e.g., aperture 842) for permitting fluid to flow into inner lumen 808 when the opening at the distal end of inner lumen 808 is blocked. Such pathway may further comprise a connection extending through inner wall 825 and outer wall 818 (see e.g., connection 528 of FIG. 5A) coupled to a conduit which is in turn coupled to a monitor 860, a gas source 170, and/or a vacuum source 124. Additional details of systems 100 through 800 are described below for insufflation gas 102, insufflation gas source 170, trocars 106-806, open gas tubing connection 120, vacuum break 166, connection 164, conduit 175, conduit 185, vacuum source 124, and surgical instrument 126.

Insufflation gas 102 may be any suitable gas used for insufflation purposes. In one example, insufflation case is carbon dioxide. Insufflation gas source 170 may be any suitable source of insufflation gas 102 at any suitable pressure.

Trocar 106, 206, 306, 406, 506, 606, 706, and 806 could be any suitable trocar that includes an inner and outer lumen as described herein. All trocars described herein may be open or closed at the distal end, as the application of the trocar would allow. Further the trocars may or may not include apertures in their inner wall separating the outer lumen from the inner lumen. Further all trocars described herein may be formed according to features described in the '219 Patent, the '112 Patent, and/or the '189 Patent. Further, trocars 106-806 may be formed with a heater and/or humidifier therein.

Vacuum break 166 may be a flapper valve that remains closed when the patient cavity is under a pressure higher than the surrounding atmosphere. The closed valve will not allow insufflation gas to leak into the atmosphere. When the pressure in patient cavity 104 drops to atmospheric pressure or lower the flapper valve 166 will open relieving most of the negative pressure within the body cavity.

Conduit 175 may be any suitable conduit for providing an insufflation gas to a portion of a trocar. An example of conduit 175 includes flexible PVC tubing.

Conduit 185 may be any suitable conduit for providing a vacuum to a portion of a trocar. An example of conduit 185 is flexible PVC tubing.

Vacuum source 124 is any suitable device that can apply a relative negative pressure to a portion of a trocar for removal of smoke from a patient cavity. Examples of vacuum source 124 include a standalone vacuum pump or a centralized hospital vacuum system.

Surgical instrument 126 may be any suitable instrument that may be used in surgery, including an obturator used to make an incision to obtain access to a body cavity.

Modifications, additions, or omissions may be made to systems 100, 200, 300, 400, 500, 600, and 700 without departing from the scope of the invention. The components of these systems may be integrated or separated. Moreover, the operations of these systems may be performed by more, fewer, or other components.

Although FIGS. 1A through 7B have been described above as including particular steps and/or components, the method and systems of FIGS. 1A through 7B may include any combination of any of the described steps and/or components and any of the options or features described herein, as would be understood by one of ordinary skill in the art. For example, any of the steps, options, or features described herein may be utilized in combination with the illustrated embodiments of FIGURES A through 7B and/or any number of the other steps, options, or features also described herein, as would be understood by one of ordinary skill in the art.

Although the embodiments in the disclosure have been described in detail, numerous changes, substitutions, variations, alterations, and modifications may be ascertained by those skilled in the art. It is intended that the present disclosure encompass all such changes, substitutions, variations, alterations, and modifications.

What is claimed is:

1. A method comprising:
  positioning a distal portion of a trocar into a patient cavity, the trocar comprising:
    an outer tubular member disposed about an inner tubular member;
    a first gas tubing connection fluidly connected to a lumen of the inner tubular member;
    a second gas tubing connection fluidly connected to a lumen of the outer tubular member; and
    a vacuum break comprising a flapper valve;
    wherein:
      the inner tubular member is formed with an opening at the distal portion and an opening at a proximal portion of the trocar, the openings being adapted to provide access to the patient cavity, wherein the inner tubular member further comprises a seal to deter the escape of gasses through a proximal portion of the inner tubular member;

the inner tubular member is separated from the outer tubular member by an inner wall;
the vacuum break is fluidly connected to the second gas tubing connection;
supplying an insufflation gas to the patient cavity through the inner tubular member via the first gas tubing connection; and
removing smoke from the patient cavity through the outer tubular member via the second gas tubing connection, wherein a vacuum source is coupled to the second gas tubing connection.

2. The method of claim 1, wherein the vacuum source further comprises a portable vacuum source.

3. The method of claim 1, wherein the vacuum source further comprises a centralized hospital vacuum system.

4. The method of claim 1, wherein the trocar further comprises a heater and a humidifier.

\* \* \* \* \*